United States Patent [19]

Whitehurst et al.

[11] Patent Number: 4,888,421

[45] Date of Patent: Dec. 19, 1989

[54] PROCESS FOR MAKING COMPOUNDS CONTAINING CHELATED METAL IONS AND RESULTANT PRODUCTS WHICH ARE USEFUL FOR AGRICULTURAL, INDUSTRIAL, ENVIRONMENTAL, AND CONSTRUCTION PURPOSES

[76] Inventors: Brooks M. Whitehurst; Garnett B. Whitehurst, both of 1983 Hoods Creek Dr., New Bern, N.C. 28560; Donald F. Clemens, 1701 Sulgrave Rd., Greenville, N.C. 27834

[21] Appl. No.: 98,317

[22] Filed: Sep. 18, 1987

[51] Int. Cl.$^4$ .............................................. C07H 23/00
[52] U.S. Cl. ...................................... 536/121; 514/23; 424/442
[58] Field of Search ........................... 536/121; 514/23; 424/442

[56] References Cited

U.S. PATENT DOCUMENTS

| | | | |
|---|---|---|---|
| 2,943,100 | 6/1960 | Holstein | 536/3 |
| 2,992,998 | 7/1961 | Karabinos et al. | 252/156 |
| 3,062,878 | 11/1962 | Karabinos et al. | 252/80 |
| 3,074,927 | 1/1963 | Saltman et al. | 536/121 |
| 3,105,822 | 10/1963 | Karabinos et al. | 252/156 |
| 3,217,034 | 11/1965 | Karabinos et al. | 252/156 |
| 3,679,659 | 7/1972 | Zak | 536/121 |

*Primary Examiner*—H. M. Sneed
*Assistant Examiner*—Chung K. Pak
*Attorney, Agent, or Firm*—Leydig, Voit & Mayer

[57] ABSTRACT

This invention discloses processes and resulting products for the manufacture of metal heptonates from saccharides via a Kiliani-Fisher reaction and subsequent reaction with the desired metal. Manganese, iron, copper zinc and magnesium heptonates are each made by a slightly different process but the resulting metal chelates provide a soluble form of the metal for agricultural, industrial, environmental and construction uses. The amount of metal chelated is directly related to the percentage of fructose in the initial monosaccharide mixture. For cations with no color, the chelating agent can be decolorized with $H_2O_2$ to give a lighter colored product providing the $NH_3$ concentration is reduced below 0.35% prior to the decolorizing step. An equivalent strong oxidizing agent may be used instead of $H_2O_2$.

18 Claims, 1 Drawing Sheet

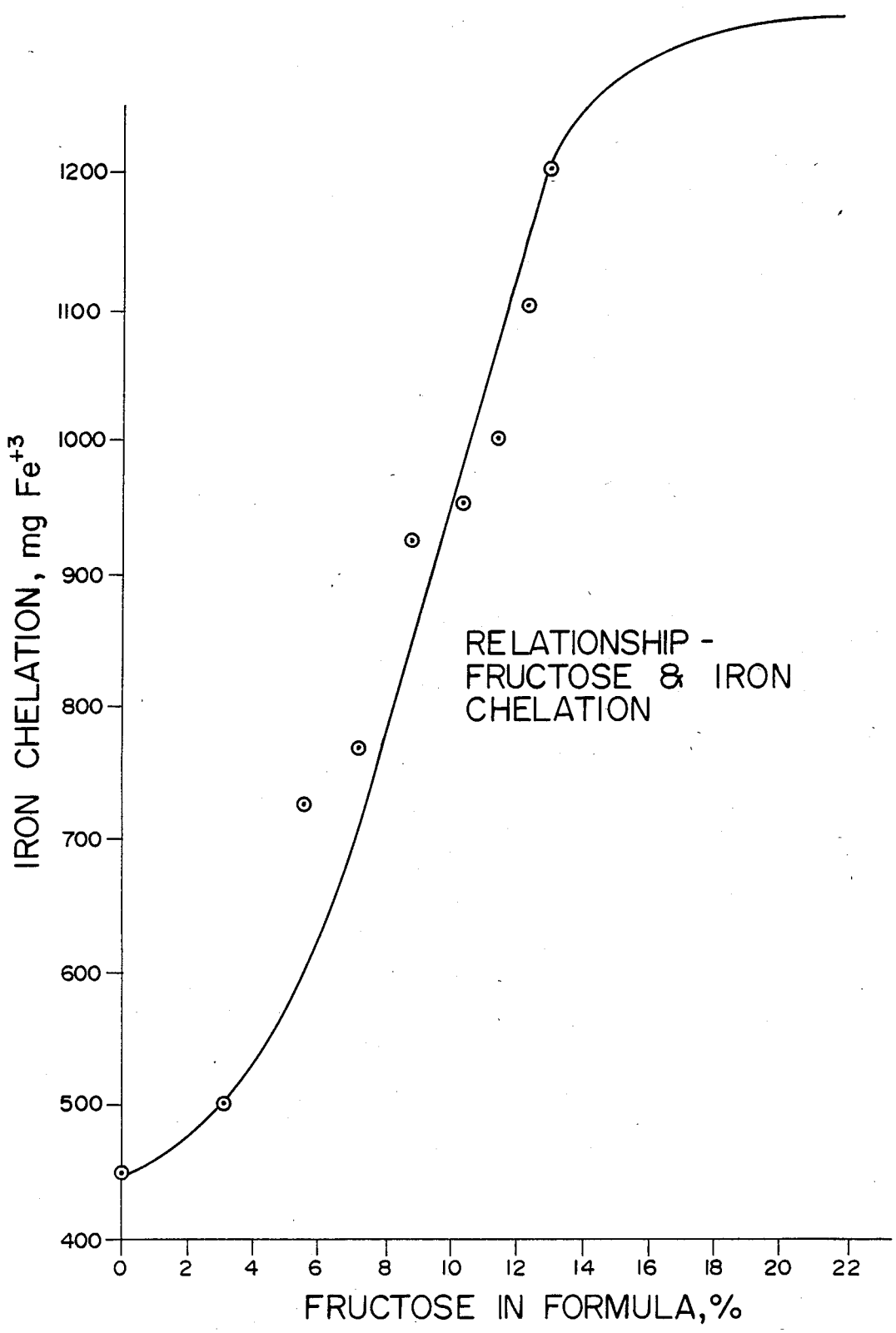

PROCESS FOR MAKING COMPOUNDS CONTAINING CHELATED METAL IONS AND RESULTANT PRODUCTS WHICH ARE USEFUL FOR AGRICULTURAL, INDUSTRIAL, ENVIRONMENTAL, AND CONSTRUCTION PURPOSES

BACKGROUND

Historically dairies, breweries, and soft drink bottlers were involved in washing glass bottles in hot caustic solutions using tap water. The metal ions, usually calcium and magnesium, in these solutions tended to form insoluble precipitates that would deposit on the glassware as well as on the equipment used. Sequestering agents known as chelates were added to the washing compounds to keep the metal ions in solution and thus, prevent the undesirable deposits from forming.

An inexpensive chelating agent that is most satisfactory for applications in solutions with a high pH is sodium glucoheptonate. This chelate is prepared by reacting glucose with sodium cyanide in a Kiliani-Fisher reaction producing a nitrile which is subsequently hydrolyzed to form the salt of glucoheptonic acid. Much research has been carried out in the last 30 years with the goal of developing inexpensive chelates that could be used in a wide variety of application.

The majority of this work centered on using 6 or 7 carbon atom sugars but price and sequestering ability made the hexoses the most common starting materials. Most inventions were aimed at the glass washing trade with the purpose of removing undesirable metal ions from the alkaline medium but Arthur Holstein perceived that compounds containing chelated metal ions would be attractive to a different market. His U.S. Pat. (No. 2,943,100) protected the methods of preparing the heavy metal salts of alpha and beta glucoheptonates. The methods presented in his disclosure involved using pentoses, hexoses, invert sugars, or the carbohydrate mixture obtained from thermally hydrolyzed lignocellulose as the starting sugars. The only mixtures of sugars that he reported resulted from hydrolyzing invert sugars. For example, cane sugar would yield equal quantities of glucose and fructose. Karabinose (U.S. Pat. No. 3,217,034) also worked with invert sugars comparing the sequestering ability of the gluconates, glucoheptonates, fructoheptonates, and equal mixtures of glucoheptonates and fructoheptonates produced from invert sugar.

This research on sugar acids led to the industrial production of large amounts of these sequestering agents that found uses in a variety of applications that ranged from cement additives and textile finish additives to bottle washing compounds. The chelated iron compound was used as a micronutrient in some agricultural applications.

PRIOR ART STATEMENT

U.S. Pat. No. 2,943,100, Holstein, teaches the manufacture of metal chelates from alkali-metal salts of sugar acids. This process uses the natural mixture of sugar acids derived by the cyanidization and subsequent hydrolysis of the nitriles formed when starting with glucose, invert sugar, or the carbohydrate mixture derived from thermohydrolytically treated lignocellulose.

U.S. Pat. Nos. 2,992,998; 3,062,878; 3,105,822; and 3,217,034 (all to Karabinos) teach the manufacture of heptonic acids from invert sugar, from fructose and from a variety of other hexose sugars.

UTILITY STATEMENT

The chelating agent formed when this invention as practiced is able to sequester metal ions at a lower cost than a similar product made from fructose or the mixture of fructose and glucose obtained from invert sugar. The chelated metal compounds that can be formed from this invention are useful as micronutrients in agriculture and animal feeds, as accelerators in cement admixtures, as micronutrients for bacteria in waste treatment plants with metal deficiencies, and as sulfide and selenide scavengers in industrial waste streams.

DESCRIPTION OF THE DRAWING

The FIGURE is a graph showing the iron chelation with fructose.

DESCRIPTION OF THE INVENTION

Sodium glucoheptonate and sodium fructoheptonate have been documented as being effective as chelating agents that sequester metal ions but it was totally unexpected to discover that the iron chelation ability of a mixture of the two was directly related to the concentration of the fructose in the starting saccharide mixture. Early experiments indicated that in the case of ferric ions, the amount of iron sequestered was directly related to the percentage of fructose as a part of the monosaccharides present in the starting mixture. The relationship is so strong that a graph of concentration versus the chelation number of iron gives practically a straight line between two and fourteen percent. The graph is presented as the FIGURE. As the concentration of fructose increases above fourteen percent, the relationship decreases and the advantage of additional fructose is offset by the higher cost of the material.

The chelating agent of this invention has been shown to sequester manganese II, iron III, copper II, and zinc II. It should be obvious that any person practiced in the art of making compounds of this type could apply this invention to a variety of other metal ions. The chelated metal compounds that can be formed from this invention are useful as micronutrients in agriculture and animal feeds, as accelerators in cement admixtures, as micronutrients for bacteria in waste treatment plants with metal deficiencies, and as sulfide and selenide scavengers in industrial waste streams. When this process is used to make the iron III or manganese II chelates, the product can be dried to remove water, leaving a water soluble solid that is readily used in a number of applications such as agricultural micronutrients, cement admixtures, animal feeds, and a variety of industrial applications. It was totally unexpected to discover that this solid was a friable easily ground material. The literature teaches that when the beta glucoheptonates are present, it is difficult or impossible to obtain a workable solid. (See U.S. Pat. No. 3,084,188 by Horn and Klein.) Undoubtedly other dried chelants could be prepared in a similar fashion.

Most commercial sugar acid chelants contain about 50% solids. When the product of this invention containing iron is prepared with 50% solids and a ratio of chelating agent to iron of two to one, the setting time of portland cement is accelerated from 140 minutes to 120 minutes. The test is run by adding 4 ounces of chelating agent to 100 pounds of cement and then measuring the time it takes for the cement to begin to set. Tests were run varying the ratio of chelant to iron from 1.5 to 1 up to 5 to 1. As the ratio increased, the acceleration effect decreased giving a preferred ratio of 2 to 1 for maximum acceleration at lowest cost.

The following six paragraphs describe methods for preparing some of the possible chelated metal products. Each is slightly different but all use the exceptional chelating ability of this invention.

In the manufacture of the chelated iron product, iron nitrate, $Fe(NO_3)_3$, is dissolved in one-half the calculated amount of the chelating agent of this invention. The other one-half of the chelating agent is added to a caustic solution of either NaOH or KOH. The iron-chelate solution is then slowly poured into the caustic solution. The pH must always be above 12 and this results in a product containing up to 6% iron with a low viscosity and a clear dark red color. This solution is miscible with water in all proportions and is miscible with liquid fertilizers, particularly the acid fertilizers. If iron sulfate is used instead of the nitrate, the highest percentage of iron that can be obtained is about 4%.

A 7% zinc heptonate can be made from zinc nitrate by adding the zinc salt to the chelating agent of this invention. Concentrated aqueous ammonia was added stoichiometrically in a four to one ratio with zinc. The mixing operation proceeds smoothly with the pH at about 4 prior to the addition of $NH_3$. As the ammonia is added, the pH rises and the solution becomes more viscous at a pH between 6 and 7. As the pH reaches 7.5 and especially at 8, the solution becomes very fluid like water. When all the ammonia is added, the final pH is about 8.5. The final product is miscible with both water and acid fertilizers. The zinc heptonate has also been made starting with pigment grade ZnO which has an extremely fine grain size. The zinc oxide is added directly to the chelating agent and the resulting solution can contain as much as 12% zinc.

Magnesium heptonate is made by dissolving magnesium carbonate in the chelating agent calculated so the final percentage of Mg is 4%. The pH exceeded 10 so a small amount of nitric acid was added to lower the pH to 8.2. This made a stable product which could readily be added to water or acid fertilizers without forming a precipitate.

The marketplace seems to want a 5% chelated calcium that also contains 0.5% boron. The product is made by adding the calculated amount of boric acid, $H_3BO_3$, to the chelating agent of this invention. After the reaction took place calcium nitrate was added yielding a solution with a pH of about 6. Aqueous ammonia was added to raise the pH to 8 and the resulting solution was miscible with water and acid fertilizers.

The manganese heptonate was made in a similar fashion to the zinc product. $Mn(NO_3)_2$ was added to an appropriate quantity of the chelating agent so the final concentration of $Mn^{2+}$ was 5%. The pH at this stage was 6 so ammonia was added to raise the pH to 9. The resulting solution was miscible with both water and acid fertilizers.

The formation of copper heptonate is different. Copper carbonate is dissolved in aqueous ammonia to form a turbid solution containing the deep blue $Cu(NH_3)_4^{2+}$. Then the chelating agent of this invention is added until the turbidity disappears. (The turbidity change is about as sharp as a titration end point.) The resulting copper heptonate solution can be made with more than 10% $Cu^{2+}$ and it is still miscible with both water and acid fertilizers.

The examples cited below indicate that the chelating agent of this invention has the ability to sequester a variety of metal ions. As mentioned previously the procedures for the formation of compounds containing chelated metal ions is somewhat different for each different metal. In the case of the iron compound, it was noted that if an iron sulfate salt was used, the percent of iron was severely restricted because a precipitate was formed. It has also been found that in the production run, the iron compound can be made by adding the caustic to the chelating agent and then adding the iron salt provided high shear agitation is used.

It has been found that when the chelated iron compound is used to treat waste streams containing sulfide ion, the rotten egg odor characteristic of hydrogen sulfide is removed and the resulting water does not contain particulate matter. There is an EDTA chelated iron compound on the market that reacts in a similar fashion except that the resulting solution contains a fine suspension of particles that are almost colloidal in nature. If a strong light is shined through the EDTA solution, the beam strikes the particles and the beam is visible. This is known as the Tyndall effect. When the chelated iron compound of this invention is used, there is no Tyndall effect, indicating a true solution is formed that contains no particulate matter.

Some markets for metal chelating agents require a product that is no darker than a typical iced tea so that upon dilution the color is very light. The Kiliani-Fisher reaction for making glucoheptonates from hexoses generally produces a product that is dark in color. The principle cause of this darkening is related to the high pH of the reaction mixture. The hydrolysis of the nitrile releases ammonia and this coupled with the exothermicity of the overall reaction results in a considerable darkening of the product. The addition of 35% hydrogen peroxide causes a significant lightening or decolorizing of the chelant. The problem with this process is that after storage for a month or two the chelating agent has darkened somewhat over the light color obtained the day the hydrogen peroxide was added. We have discovered that the controlling factor is the presence of ammonia in the chelating agent. If the ammonia is reduced below 0.35%, and preferably below 0.25%, and then the chelating agent is decolorized by the addition of hydrogen peroxide, the resulting color is stable and the product can be stored for an extended period of time with little or no change in the color. The lowering of the ammonia concentration is accomplished by a variety of methods but most important is sparging with air at a high pH. This is accomplished by adding sodium hydroxide and sparging with air to sweep the ammonia out of the solution. After the ammonia has been removed, the pH is about 11 and the hydrogen peroxide is added until the desired color is obtained. At this point the pH is about 8 and is lowered to between 6 and 6.5 with nitric acid. We have made the decolorized chelating agent and stored it for six months in a fiberglass tank with no perceptible change in color.

EXAMPLES

EXAMPLE 1

The chelating agent with an 11.6% fructose concentration was prepared by mixing 121 g of 32 DE corn syrup with 180 g 43% fructose corn syrup (the balance being glucose). A quantity of NaCN in the amount of 36.0 g was added to 136 g of water and this solution was then slowly added to the sugar solution. After the exothermic reaction took place the solution was heated to remove the NH₃ that formed in the hydrolysis of the nitrile.

EXAMPLE 2

The chelating agent with a 10.1% fructose concentration was prepared by mixing 158 g of 32 DE corn syrup with 169 g of 43% fructose corn syrup. The solution was diluted with 139 g of water and then 36.0 g of NaCN was stirred into the mixture. After the reaction took place the mixture was heated to remove the ammonia and then allowed to cool.

EXAMPLE 3

The scaled up production of the chelating agent with 12.96% fructose was carried out by mixing 14,271.2 pounds of beet molasses containing 2,489.6 pounds of fructose with a 4,936.6 pounds of fructose corn syrup containing 1,507.2 pounds of fructose. 9,421 pounds of water was added and then 2,205 pounds of sodium cyanide was mixed into the solution. After the temperature peaked, the reaction mixture was heated until most of the ammonia was removed from the solution.

EXAMPLE 4

In another production run, 18,552 pounds of beet molasses containing 3,236.5 pounds of fructose was mixed with 2,504.2 pounds of fructose syrup containing 764.5 pounds of fructose. This mixture was then diluted with 9,146.8 pounds of water and then 2,205 pounds of sodium cyanide was added to give a chelating agent containing 12.35% fructose.

EXAMPLE 5

The chelated manganese compound was prepared by adding 2600 pounds of 50% manganese nitrate to 4253 pounds of the chelating agent of this invention. The pH was raised by the addition of 645 pounds of 50% NaOH and 511 pounds of water was added to adjust the final concentration to 5.0% manganese.

The chelated zinc compound was prepared by adding 1608 pounds of 26.5% NH₃ to 2923 pounds of the chelating agent of this invention. At this point the pH of the solution was 11.7. The pH dropped to 8.2 when 1900 pounds of zinc chloride and 755 pounds of water was added to the solution The final product contained 6.6% zinc.

EXAMPLE 7

A 7.4% zinc product can also be made using zinc nitrate or even zinc oxide. For instance, 40.0 g of water was mixed with 39.1 g of 50% sodium hydroxide and 18.1 g of zinc oxide. Then the temperature was raised to 100° C. and the solution was mixed with 100.0 g of the chelating agent of this invention. This solution had a pH of 13 and when mixed with liquid fertilizers gave a clear solution.

EXAMPLE 8

A 4.7% iron product was made in a production run by mixing 8867 pounds of 39% FeCl₃ with 4244 pounds of the chelating agent. In another vessel, 4244 pounds of the chelating agent was added to 6062 pounds of 50% NaOH. The chelate-iron solution was then added to the caustic-chelate solution, and after the exothermic reaction had taken place, the pH was 12.5 so 476 pounds of 93% H₂SO₄ was added to lower the pH to 8.2.

EXAMPLE 9

A 5.7% iron product was made by mixing 150.5 g Fe(NO₃)₃ with 26.0 g of the chelating agent and in a separate beaker adding 26 g of chelating agent to 90.0 g of 50% NaOH. The chelate-iron solution was the added to the chelate-caustic solution, and the pH was lowered to 8.2 by the addition of 14.5 of 66% HNO₃.

EXAMPLE 10

An 8.0% copper product was made by mixing 33.0 pounds of copper carbonate containing 55% Cu with 74.7 pounds of 26.5% ammonia. Then 23.9 pounds of water was added to dilute the solution and 70.2 pounds of the chelating agent was added carefully until the turbidity just disappeared. The pH was lowered to 8.5 by the addition of 26.5 pounds of 66% HNO₃. The resulting solution was a clear green color.

EXAMPLE 11

The chelating agent with a 3.4% fructose concentration was prepared by mixing 7,428 pounds of beet molasses containing 2,443 pounds of fructose with 2,006.0 pounds of 38 DE corn syrup. The mixture was diluted with 13,320 pounds of water and then 1,774 pounds of sodium cyanide was added.

EXAMPLE 12

The chelating agent with 6.3% fructose concentration was prepared by mixing the 144 grams of a 43% fructose corn syrup with 341 grams of 32 DE corn syrup. The mixture was diluted with 164 grams of water and then 36.0 grams of sodium cyanide was added. After the temperature stopped climbing from the exothermic reaction, 20.0 g of boric acid was added. The resulting chelating agent was tested by the procedure of Mehltretter et al. (C. L. Mehltretter, B. H. Alexander, and C. E. Rist, SEQUESTRATION BY SUGAR ACIDS, Industrial and Engineering Chemistry, 45, 2782, 1953) and for each gram of chelant 750 milligrams of $Fe^{+3}$ was sequestered in a solution containing 3% NaOH.

EXAMPLE 13

A straw colored chelating agent is prepared by mixing 33,719 pounds of 28 DE corn syrup with 12,070 pounds of water and 1,323 pounds of sodium cyanide. As the temperature from the exothermic reaction begins to fall, air is bubbled through the solution and the temperature is increased to about 90° C. After 24 hours the reaction mixture is cooled, and the ammonia concentration is 0.35% or less. At this time, 3,053 pounds of hydrogen peroxide is added to the solution which again results in an increase in temperature. As this reaction proceeds, oxygen is given off from the decomposition of the excess hydrogen peroxide. The evolution of tiny bubbles of oxygen sweeps more ammonia from the solution until the final concentration reaches 0.25%. The pH is then lowered to 6.2 by the addition of 250 pounds of 66% nitric acid. This straw colored solution would be expected to be color stable for a period of time in excess of six months.

EXAMPLE 14

A weak iced tea colored chelating agent is prepared by mixing 33,719 pounds of 28 DE corn syrup with 12,070 pounds of water and 1,323 pounds of sodium cyanide. The solution is sparged with air to remove some of the ammonia and then 3,053 pounds of hydrogen peroxide is added to decolorize the chelating agent. When the reaction mixture cools, it is pumped to a fiberglass storage tank. This light colored material begins to darken after about one month and continues to darken until after six months the color is a deep wine red.

We claim:

1. A method of producing chelated metal from ions of a metal selected from the group consisting of: manganese II, iron III, iron II, copper II, zinc II, calcium, and magnesium II, which comprises contacting said metal ions with a heptonate chelating agent containing about 10–14% by weight of fructose, mixing said chelating agent and said metal ions and raising the pH of the resulting mixture to an alkaline pH.

2. A method of claim 1 wherein the selected metal ion is $Fe(NO_3)_3$ or $Fe_2(SO_4)_3$ or $FeCl_3$ and said mixing comprises adding said selected metal ion slowly to said chelating agent with high shear mixing, said chelating agent being combined with caustic solution to maintain the overall pH of the resulting mixed solution at least 12.

3. A method of claim 2 wherein the selected metal ion is dissolved in one-half the chelating agent prior to said mixing with the caustic solution containing the other one-half of the chelating agent.

4. A method of claim 1 wherein zinc ion is reacted with ammonia prior to said mixing.

5. A method according to claim 1 wherein manganese heptonate is initialy formed at pH 6 in the mixing stage prior to said raising the pH.

6. A method of claim 1 wherein copper heptonate is formed by dissolving copper carbonate in aqueous ammonia to form a turbid intermediate prior to said mixing and then subjecting said turbid intermediate to said mixing comprising adding the heptonate chelating agent until the turbidity of said intermediate disappears, resulting in a copper heptonate solution.

7. The method of claim 1 wherein said mixing comprises dissolving magnesium carbonate in the chelating agent so that the final percentage of magnesium is 4% by weight and the alkaline pH of the resulting solution is kept below 10.

8. The method of claim 1 wherein said chelating agent is prepared by providing the percentage of ammonia to less than 0.35% by weight prior to oxidizing with $H_2O_2$ and then lowering the pH of the resulting solution to below 7.

9. The method of claim 1 wherein the resulting chelated metal product is dehydrated by drying to yield a friable, water-soluble solid.

10. A process for producing a chelated iron product from an iron ion comprising:
    (a) adding an amount of said iron ion to a chelating agent, said amount being in a ratio of about 1.5:1 to about 5:1 of chelant to iron, said chelating agent being a heptonate containing 10–14% by weight of fructose;
    (b) adding the chelating agent used in step (a) to a caustic hydroxide solution; and
    (c) slowly adding the product of step (a) to the solution of step (b), under conditions wherein the pH of the resulting mixture is maintained above 12.

11. The process of claim 10 wherein said iron ion is iron sulfate.

12. The process of claim 10 wherein said iron ion is iron nitrate.

13. The process of claim 10 wherein said iron ion is iron chloride.

14. The process of claim 10 wherein said chelating agent is made by the Kiliani-Fisher reaction.

15. The process of claim 10 wherein said caustic hydroxide solution is sodium hydroxide or potassium hydroxide.

16. The process of claim 11 wherein the chelated iron product has low viscosity and contains about 6% by weight iron.

17. The process of claim 12 wherein the chelated iron product has low viscosity and contains about 4% by weight iron.

18. The process of claim 13 wherein the chelated iron product has low viscosity and contains about 6% by weight iron.

* * * * *